United States Patent
Doty et al.

(10) Patent No.: US 8,100,899 B2
(45) Date of Patent: Jan. 24, 2012

(54) COMBINED ENDOCARDIAL AND EPICARDIAL MAGNETICALLY COUPLED ABLATION DEVICE

(75) Inventors: John Richard Doty, Sandy, UT (US); Jeffrey L. Anderson, Salt Lake City, UT (US)

(73) Assignee: IHC Intellectual Asset Management, LLC, Salt Lake City, UT (US)

( * ) Notice: Subject to any disclaimer, the term of this patent is extended or adjusted under 35 U.S.C. 154(b) by 855 days.

(21) Appl. No.: 11/938,700

(22) Filed: Nov. 12, 2007

(65) Prior Publication Data
US 2009/0124847 A1      May 14, 2009

(51) Int. Cl.
*A61B 18/14*      (2006.01)
(52) U.S. Cl. .................... 606/41; 606/49; 606/50
(58) Field of Classification Search .......... 606/32–50; 607/101–105, 115–116
See application file for complete search history.

(56) References Cited

U.S. PATENT DOCUMENTS

| | | | | |
|---|---|---|---|---|
| 4,004,298 | A * | 1/1977 | Freed | 623/3.1 |
| 5,429,131 | A * | 7/1995 | Scheinman et al. | 600/374 |
| 6,292,678 | B1 * | 9/2001 | Hall et al. | 600/374 |
| 6,314,963 | B1 * | 11/2001 | Vaska et al. | 128/898 |
| 6,527,767 | B2 * | 3/2003 | Wang et al. | 606/32 |
| 6,899,710 | B2 | 5/2005 | Hooven | |
| 6,932,811 | B2 | 8/2005 | Hooven et al. | |
| 6,974,454 | B2 | 12/2005 | Hooven | |
| 7,113,831 | B2 | 9/2006 | Hooven | |
| 7,211,082 | B2 * | 5/2007 | Hall et al | 606/41 |
| D544,602 | S | 6/2007 | Hughett, Sr. et al. | |
| 7,229,469 | B1 * | 6/2007 | Witzel et al. | 607/113 |
| 7,288,092 | B2 | 10/2007 | Hooven | |
| 7,291,161 | B2 | 11/2007 | Hooven | |
| 7,487,780 | B2 | 2/2009 | Hooven | |
| 7,530,980 | B2 | 5/2009 | Hooven | |
| 7,582,086 | B2 | 9/2009 | Privitera et al. | |
| 2005/0187545 | A1 * | 8/2005 | Hooven et al. | 606/41 |
| 2005/0203561 | A1 | 9/2005 | Palmer et al. | |
| 2005/0203562 | A1 | 9/2005 | Palmer et al. | |

(Continued)

FOREIGN PATENT DOCUMENTS
EP          1 880 687          1/2008

(Continued)

OTHER PUBLICATIONS

Gillinov et al., "Atrial Fibrillation: Current Surgical Options and Their Assessment", *Ann Thorac Surg*, vol. 74, pp. 2210-2217, 2002.

(Continued)

*Primary Examiner* — Michael Peffley
*Assistant Examiner* — Daniel Fowler
(74) *Attorney, Agent, or Firm* — Stoel Rives LLP

(57) ABSTRACT

A device for automatically aligning bipolar electrodes on opposing sides of operative tissue is provided for performing minimally invasive RF ablation. The device includes complementary magnetic electrode assemblies, each having a permanent magnet mechanically coupled to and electrically insulated from an electrical conductor. When positioned on opposing sides of tissue such as an atrial wall, the complementary assemblies automatically align their respective electrical conductors through mutual magnetic attraction to complete an electrical circuit. Each electrical conductor may provide an alignable elongated transmitting element adjacent to a magnetic coupling surface to allow for ablation of linear segments of tissue. Each electrode assembly includes mechanical linkage for coupling to an intracorporeal positioning device and a wire receiving terminal for connection to an external generator.

23 Claims, 5 Drawing Sheets

U.S. PATENT DOCUMENTS

| | | | |
|---|---|---|---|
| 2006/0069385 A1 | 3/2006 | Lafontaine et al. | |
| 2006/0106375 A1* | 5/2006 | Werneth et al. | 606/32 |
| 2006/0149121 A1 | 7/2006 | Hughett et al. | |
| 2006/0161147 A1 | 7/2006 | Privitera et al. | |
| 2006/0161149 A1 | 7/2006 | Privitera et al. | |
| 2006/0161151 A1 | 7/2006 | Privitera et al. | |
| 2006/0167478 A1 | 7/2006 | Miller et al. | |
| 2007/0185477 A1 | 8/2007 | Hooven | |
| 2007/0191826 A1 | 8/2007 | Park et al. | |
| 2008/0009853 A1 | 1/2008 | Martin et al. | |
| 2008/0114350 A1 | 5/2008 | Park et al. | |
| 2008/0172048 A1 | 7/2008 | Martin et al. | |
| 2008/0243141 A1 | 10/2008 | Privitera et al. | |
| 2008/0275446 A1 | 11/2008 | Messerly | |
| 2008/0319440 A1 | 12/2008 | Richardson et al. | |
| 2009/0012545 A1 | 1/2009 | Williamson, IV et al. | |
| 2010/0004661 A1* | 1/2010 | Verin et al. | 606/129 |

FOREIGN PATENT DOCUMENTS

| | | |
|---|---|---|
| EP | 1 943 973 | 7/2008 |
| WO | 00/69353 | 11/2000 |
| WO | 01/80724 | 11/2001 |
| WO | 03/037162 | 5/2003 |
| WO | 2007/100754 | 9/2004 |
| WO | 2004/093659 | 11/2004 |
| WO | 2005/081868 | 9/2005 |
| WO | 2005/104972 | 11/2005 |
| WO | 2005/110205 | 11/2005 |
| WO | 2006/055166 | 5/2006 |
| WO | 2006/073582 | 7/2006 |

OTHER PUBLICATIONS

Benussi et al., "Surgical Ablation of Atrial Fibrillation with a Novel Bipolar Radiofrequency Device", *J Thorac Cardiovasc Surg*, vol. 130, No. 2, pp. 491-497, Aug. 2005.

Wolf et al., "Video-assisted Bilateral Pulmonary Vein Isolation and Left Atrial Appendage Exclusion for Atrial Fibrillation", *J Thorac Cardiovasc Surg*, vol. 130, No. 3, pp. 797-802, Sep. 2005.

Doty et al., Comparison of Standard Maze III and Radiofrequency Maze Operations for Treatment of Atrial Fibrillation, *J Thorac Cardiovasc Surg*, vol. 133, No. 4, pp. 1037-1044, Apr. 2007.

"RF Ablation" www.bostonscientific.com, 2 pages, Aug. 14, 2007.

Saltman, Adam E. "Completely Endoscopic Microwave Ablation of Atrial Fibrillation on the Beating Heart Using Bilateral Thoracoscopy", www.ctsnet.org, 10 pages, Sep. 4, 2007.

"Maze procedure" www.wikipedia.org, 5 pages, Sep. 9, 2007.

\* cited by examiner

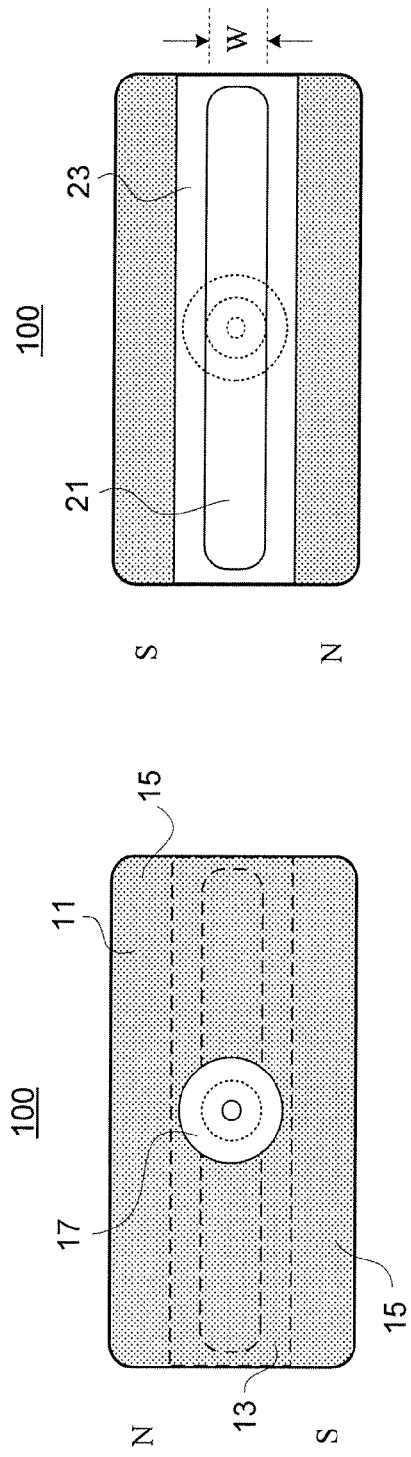
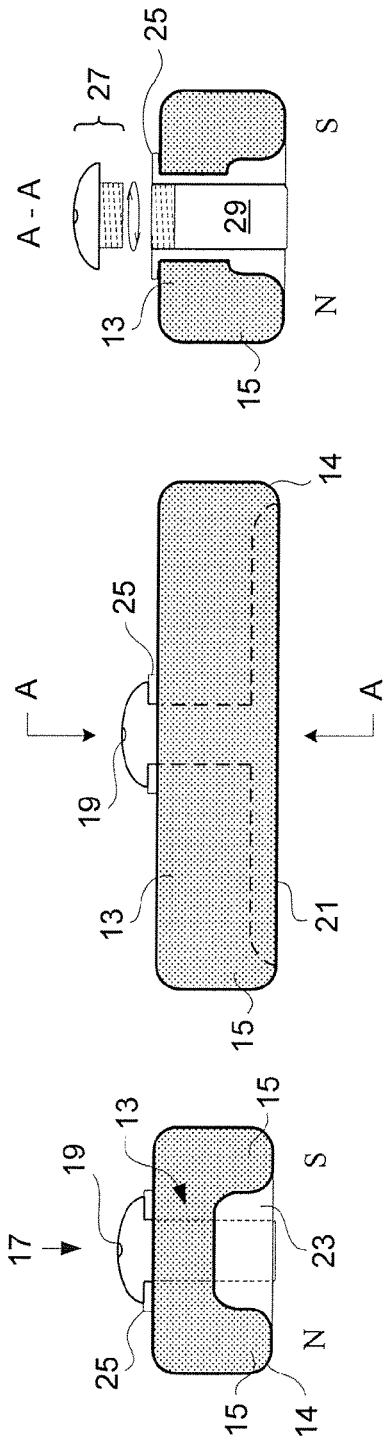

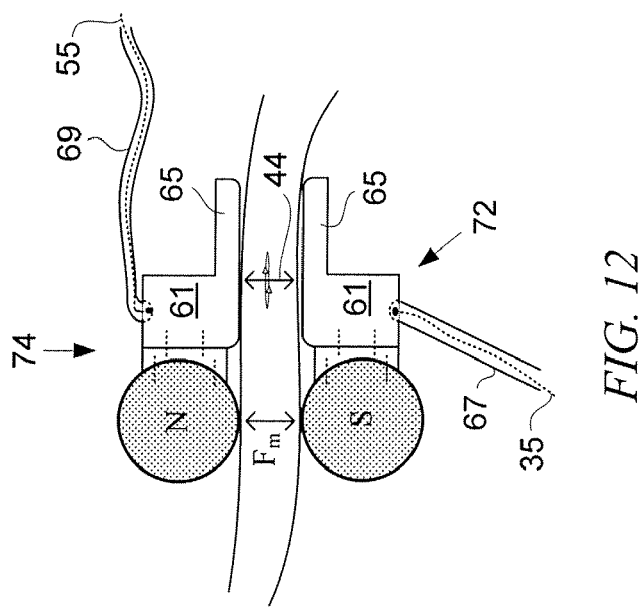
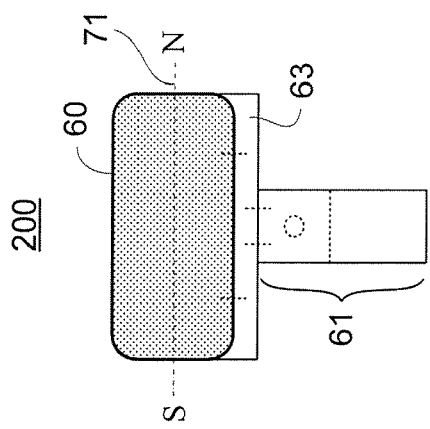
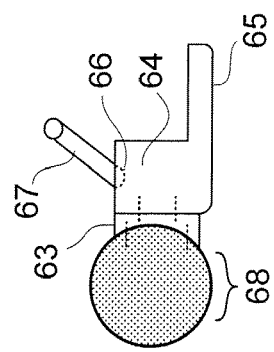
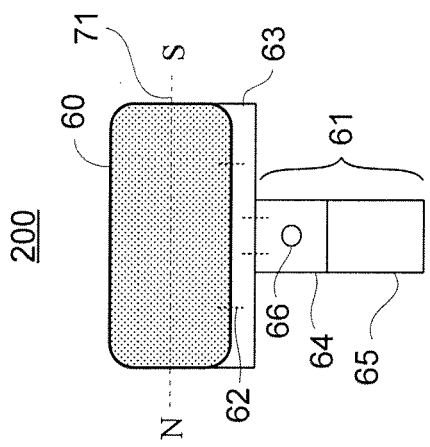
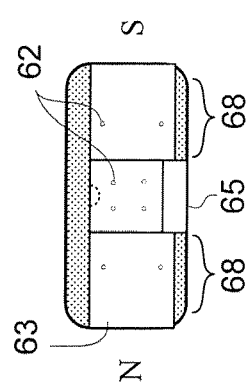

COMBINED ENDOCARDIAL AND EPICARDIAL MAGNETICALLY COUPLED ABLATION DEVICE

BACKGROUND OF THE INVENTION

1. Field of the Invention

The present invention relates generally to surgical ablation. More specifically, the invention relates to a system for aligning bipolar electrodes for radiofrequency ablation, and most specifically to a system for automatically aligning bipolar electrodes on the atrial wall for treating atrial fibrillation by transmural radiofrequency ablation.

2. Description of Related Art

Atrial fibrillation ("AF") is a heart disease that affects one to two percent of the population of the United States. It is estimated that at any given time, about 2 million people in the United States experience some form of AF, and about 160,000 new cases are diagnosed annually. The prevalence of AF and the health risks associated with it increase with age.

In a patient with AF, the electrical impulses that are normally generated by the sinoatrial node are overwhelmed by disorganized electrical activity in the atrial tissue, leading to an irregular conduction of impulses to the ventricles that generate the heartbeat. The result is an irregular heartbeat, which may be intermittent or continuous. In human populations, AF-induced irregular heartbeat is a significant source of stroke, heart failure, disability, and death.

There are a number of surgical options available for treating AF. One approach pioneered by Dr. James Cox and associates was first performed in 1987, and after several refinements, has evolved into what is now widely known as the Cox-Maze III procedure. In this procedure, the left atrial appendage is excised, and a series of incisions and/or cryolesions are arranged in a maze-like pattern in the atria. The incisions encircle and isolate the pulmonary veins. The resulting scars block the abnormal electrical pathways, improving normal signal transmission and restoring regular heart rhythm. While the success rate is relatively good, the Cox-Maze III and variations thereof are complex open-heart surgeries, requiring cardiopulmonary bypass, median sternotomy, and endocardial incisions that require suturing of the atria. The risk of complications from Cox-Maze III remains significant.

More recently, less invasive techniques have been proposed that use heating or cooling sources to create impulse-blocking lesions on the heart by ablation rather than incision. For example, a procedure known as microwave minimaze, which may be performed epicardially, uses microwave energy to destroy electrical pathways in the atria by heating the tissue at the resonant frequency of the water molecule. In this procedure, small incisions are made on each side of the chest for inserting surgical tools and an endoscope. A flexible microwave antenna is moved along guide catheters into position behind the heart and energized. Aided by the endoscope, the surgeon guides the antenna along the atria to create the pattern of lesions around the pulmonary veins. Clinical research indicates that microwave ablation has a relatively high success rate of about 80%, and allows for the creation of transmural rather than superficial scars. However, the resonance effect of the microwave can be difficult to control, resulting in variable scar formation, and can cause unwanted damage to surrounding tissue.

Other ablation techniques have been developed that use a combination of incisions, cryoablation, and unipolar or bipolar radiofrequency ("RF") energy to create the pattern of lesions achieved in the original Cox maze procedure. The cryoablation technique per se has seen limited use due to the rigidity of the cryoprobes and to the technical difficulties inherent in the procedure. Unipolar systems have been used successfully in epicardial procedures on a beating heart. However, the transmural lesions created using a unipolar electrode are difficult to control due to the composition of the diseased atrial wall and to the effects of convective cooling from blood flow through the atria. The unipolar RF technique has also been used for ablation in endocardial procedures with somewhat elevated risk factors. Endocardial ablation has been associated with unwanted perforation of surrounding organs, due mainly to the difficulty of achieving consistent burn penetration.

Whether epicardial or endocardial, the unipolar procedure is inherently challenging because it requires that the surgeon move the electrode from point to point and effectively connect the dots to create a desired burn path. If the electrode is moved too slowly, prolonging the burn time at any one point, excessive tissue may be destroyed. If the electrode is moved too quickly along the burn path, or if it is inaccurately placed, gaps may occur in the lesion scar and the abnormal electrical pathways that cause AF may not be completely interrupted. In the latter case, a surgeon may need to repeat the maze procedure one or more times, thereby multiplying the risk factors. In about half of all cases, a surgeon must repeat the ablation procedure one or more times to achieve the desired results.

Bipolar RF ablation is becoming more common. It is effective in creating transmural scars and among all procedures has the best current success rate of about 80% to 90% for treating AF. Many problems, however, can arise from this procedure and lead to further complications. The electrodes used for bipolar ablation are typically clamps, which can be placed on the inside or outside of the atrium to burn a lesion into the clamped area of tissue. Use of the clamp on the inside atrial wall, however, requires opening the atrium to accommodate the clamp. The use of two point electrodes in a bipolar procedure is considered impractical for transmural ablation, as the surgeon would need to effect simultaneous placement of an endocardial and an epicardial probe, and maintain precise control over the speed and placement of the electrodes. If the placement pattern is inaccurate, an excessive amount of atrial tissue may lie within the burn path, and result in unnecessary destruction of tissue.

Some of the more serious complications that can arise from any of the foregoing ablation procedures are those caused by time dependent deep heating through excessive heat transfer. A perforation of the atrial wall due to excessive heating can cause permanent structural damage to the heart, or to the heart and to surrounding tissue. In one scenario, a perforation of the heart can cause a pericardial effusion or cardiac tamponade, which can be fatal without immediate evacuation of the pericardial cavity and corrective surgery. In another scenario, excessive heat transmitted by RF energy or microwaves can permeate the thin wall of the left atrium and fuse it with the esophagus, forming a fistula between the two organs. This creates a pathway into the heart for bacteria from the esophagus, posing a significant risk of infection, endocarditis, systemic sepsis, and mediastinitus outside the heart and in the heart itself. Excessive burning can also injure the endothelium, causing a blood clot that can embolize and lodge in another blood vessel or in the brain and cause a stroke or heart attack.

More recently, to minimize the risk of esophageal injury from excessive heat transfer, complex safety precautions are employed in conjunction with unipolar RF ablation. These include the use of proton pump inhibitors, fluid hydration, esophageal mapping, imaging, temperature monitoring, and energy delivery optimization. To optimize energy delivery, lesions are created by applying higher power over a shorter time period to the ablation site. For example, one technique employs a point electrode mounted in an irrigated catheter tip. The electrode is energized with a continuous RF current to deliver about 50 Watts to the ablation site, and the catheter is dragged across the atrial wall for a duration of about 2-5 seconds. The short duration minimizes the risk of time dependent deep heating. However, the surgeon must pass the electrode along the same lesion path multiple times to achieve a desired result, and must wait about two minutes between each pass. This undesirably prolongs the procedure.

What is needed to improve the efficacy of surgical and interventional vascular treatment for AF is a more reliable and less invasive means for controlling the RF energy during ablation of the atrial tissue.

SUMMARY OF THE INVENTION

The present invention provides a minimally invasive means for aligning bipolar electrodes on opposing sides of operative tissue to improve the reliability of RF ablation. The device includes a set of first and second complementary magnetic electrode assemblies. Each electrode assembly includes a permanent magnet mechanically coupled to and electrically insulated from an electrical conductor. When positioned on opposing sides of tissue such as an atrial wall, the complementary magnetic electrodes automatically align their respective electrical conductors through mutual magnetic attraction to complete an electrical circuit. Each electrode assembly may be mechanically coupled to a positioning device such as an intravenous or percutaneous catheter, and each may include means for attaching a transmission wire through the positioning device to the electrical conductor.

In one embodiment, the permanent magnet may be formed as a U-shaped trough from iron or other magnetic material. The U-shaped trough has a cross-member connecting two substantially parallel legs, with a north pole occurring on one end of the U and a south pole occurring on the other end of the U. The electrical conductor passes through the trough in a direction parallel to the legs of the U. Along the contacting surface of the electrode assembly, the electrical conductor connects to a transmitting element that may form an elongated conductive segment running midway between and parallel to the ends of the U. The magnetic coupling surface provides a smooth tissue contacting surface to facilitate translation and positioning of the assembly along the surface of the operative tissue by means of an intracorporeal positioning device that is mechanically linked to the assembly.

In another embodiment, each complementary electrode assembly has a substantially cylindrical bar magnet with north and south poles at opposite ends of a longitudinal axis. An electrical conductor is mechanically coupled to and electrically insulated from the cylindrical magnet. The electrical conductor has a wire receiving terminal on one surface and a transmitting element on a tissue contacting surface. The transmitting element may form an elongated conductive segment that is substantially parallel to the longitudinal axis. A mechanical linkage couples the assembly to an intracorporeal positioning device. Bearings may be provided to allow one or both of the cylindrical bar magnets to rotate with respect to the electrical conductor so that a surgeon can position the electrode to a desired location by rolling it along the surface of the operative tissue.

In any embodiment of the invention, when complementary electrodes are positioned on opposite sides of the operative tissue, magnetic forces align the north pole of one assembly opposite the south pole of the other assembly, causing the transmitting elements to properly align on opposite sides of the tissue. In an ablation procedure, this alignment allows transmission of RF current between the electrodes for burning a lesion into the tissue along a line having a length corresponding to the length of the transmitting elements. One electrode may be linked to a rigid positioning device while the complementary electrode may be linked to a flexible positioning device, so that when only the rigidly linked electrode is manipulated by a surgeon, the flexibly linked electrode automatically tracks the rigidly linked electrode to maintain dynamic alignment. In one embodiment, the set of electrode assemblies includes an endocardial electrode having a rigid positioning device and an epicardial electrode having a flexible positioning device. In another embodiment, the set of electrode assemblies includes an epicardial electrode having a rigid positioning device and an endocardial electrode having a flexible positioning device.

BRIEF DESCRIPTION OF THE DRAWINGS

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims. Component parts shown in the drawings are not necessarily to scale, and may be exaggerated to better illustrate the important features of the invention. In the drawings, like reference numerals designate like parts throughout the different views, wherein:

FIG. 1 is a top view of one embodiment of a magnetic electrode assembly for performing RF ablation according to the invention, wherein the magnetic core forms a slideable U-shaped trough.

FIG. 2 is a bottom view of the magnetic electrode assembly of FIG. 1.

FIG. 3 is an end view of the magnetic electrode assembly of FIG. 1

FIG. 4 is a side view of the magnetic electrode assembly of FIG. 1.

FIG. 5 is a cross-sectional side view of the magnetic electrode assembly of FIG. 1 taken along section A-A.

FIG. 8 is a top view of another embodiment of a magnetic electrode assembly for performing RF ablation according to the invention, wherein the magnetic core forms a slideable cylindrical bar magnet.

FIG. 9 is a bottom view of the magnetic electrode assembly of FIG. 8.

FIG. 10 is an end view of the magnetic electrode assembly of FIG. 8.

FIG. 11 is a side view of the magnetic electrode assembly of FIG. 8.

FIG. 12 is a side view of a magnetically coupled device having cylindrical bar magnets according to the invention positioned for transmural ablation of an atrium. An endocardial electrode is shown contacting the atrial wall and aligned with and facing an epicardial electrode that is contacting an opposite side of the atrial wall.

DETAILED DESCRIPTION OF THE INVENTION

Figure 7:
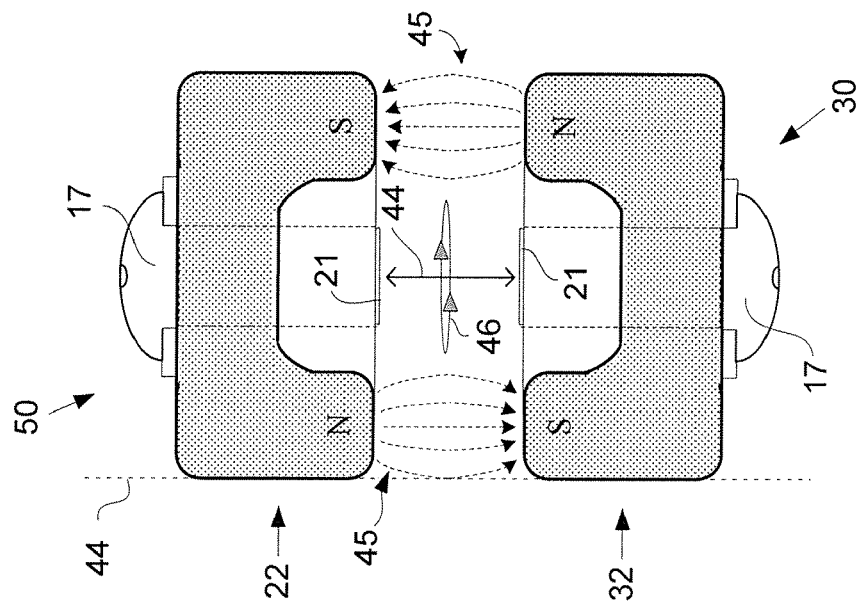
FIG. 7 is a magnified side view of the device of FIG. 6, showing the direction of magnetic flux lines of the permanent magnets with respect to the direction of magnetic flux lines created by current flow in central conductors.

The following disclosure presents various embodiments of the invention for providing automatically aligning bipolar electrodes on opposing sides of operative tissue. While a primary motivation for the invention arises from a need to improve precision and efficacy of transmural ablation in the treatment of AF, the invention is not limited to any specific procedure. The apparatus and methods disclosed herein may be applied to any surgical procedure that requires precision alignment of two or more transmitting elements across a tissue mass for the purpose of scoping, suturing, burning, cutting, freezing, excising or otherwise treating the tissue. Applications for the invention include, but are not limited to, endometrial abalation, tumor ablation, treatment of WPW syndrome, and placement of catheters, pacemakers, imaging devices, biosensors, and prostheses.

A device according to the invention includes a set of first and second complementary magnetic electrode assemblies. Each electrode assembly includes a magnetic core mechanically coupled to and electrically insulated from an electrical conductor. At least one of the magnetic cores may be a permanent magnet, while the magnetic core of the complementary assembly may be a permanent magnet or a demagnetized ferromagnetic material. When positioned on opposing sides of tissue such as an atrial wall, the complementary magnetic electrodes automatically align their respective electrical conductors through mutual magnetic attraction to complete an electrical circuit. Each electrode assembly may be mechanically coupled to a positioning device such as an intravenous or percutaneous catheter, and each may include means for attaching a transmission wire through the positioning device to the electrical conductor. By using this invention, a surgeon need only manipulate one of the magnetic electrode assemblies, as movement thereof urges the complementary electrode into automatic alignment through mutual magnetic attraction.

Throughout the disclosure, terms such as "top" and "bottom" are used to describe the relative location of parts as viewed by a reader observing the drawings. These terms are used for illustrative purposes only, and are not intended to place limitations on the orientation of any part. Terms such as "right atrium" and "left atrium" are used in their customary sense to indicate specific heart chambers viewed from the perspective of the patient.

FIG. 1 shows a top view of one embodiment of a magnetic electrode assembly 100 for performing RF ablation according to the invention. In this embodiment, electrode assembly 100 includes a magnetic core 11 in the form of a slideable U-shaped trough with a cross member portion 13 connecting two substantially parallel leg sections 15. The end of one leg 15 corresponds to the north magnetic pole N and the end of the other leg 15 corresponds to the south magnetic pole S. Magnetic core 11 may be formed from any magnetic material such as iron, cobalt, nickel, ceramic composite, alnico, lanthanoid, samarium-cobalt, neodymium-iron-boron, etc., or any combination thereof, by any suitable technique such as casting, molding, sintering, stacking, etc. Assembly 100 can be further understood with reference to the bottom view of FIG. 2, the end view of FIG. 3, the side view of FIG. 4, and the cross-sectional end view of FIG. 5.

Assembly 100 further includes an electrical conductor 17 that is bonded to and electrically insulated from magnetic core 11. Conductor 17 may be formed from any conductive material such as copper, aluminum, steel, silver, gold, etc. In the embodiment shown, conductor 17 penetrates magnetic core 11 through cross-member 13. Conductor 17 includes a wire receiving terminal 19 on the top side of the assembly, and a transmitting element 21 on the bottom side of the assembly. Wire receiving terminal 19 may be a soldering point, soldering post, male connector, female connector, plug, socket, crimp site, or other means for terminating a wire or other conductive element to conductor 17.

The bottom side of electrode assembly 100 is also referred to herein as the tissue contacting surface. At the tissue contacting surface, conductor 17 forms transmitting element 21. In the embodiment shown, transmitting element 21 forms an elongated conductive segment that is exposed along the tissue contacting surface and lies in a direction parallel to the magnetic coupling surface. In other embodiments, the elongated conductive segment may lie in a direction not parallel to the magnetic coupling surface, or may have some degree of curvature, depending on the application. The width W of the transmitting element may be on the order of about 1 mm or less. As the transmitting element 21 is drawn along a tissue wall, it may be energized to deliver electrical current through the atrial tissue until a burn scar develops wherever element 21 contacts the tissue. After one or more passes, the resulting burn scar may be made wide enough to interrupt abnormal electrical pathways in the atrium in the same way that an excision scar interrupts those pathways in a conventional maze procedure. Conversely, the width W must be sufficiently narrow to prevent unnecessary damage to the tissue. With the electrode assembly 100 energized in a fixed position against operative tissue, an elongated conductive transmitting element 21 advantageously creates a linear ablation without the surgeon having to move the assembly from point to point.

An insulator 23 provides electrical insulation between magnetic core 11 and conductor 17. Insulator 23 may be any biocompatible dielectric material suitable for this purpose. In the embodiment shown, insulator 23 includes a flanged end 25 to insulate the top surface of magnetic core 11 from a top portion of conductor 17 that contains the wire receiving terminal 19. The remainder of insulator 23 may be formed or molded for compression fit within the volume between magnetic core 11 and conductor 17, as shown. In one embodiment, conductor 17 may be formed from two mating parts to facilitate assembly—a top portion 27 and a lower portion 29. For example, electrode assembly 100 may be assembled by compression-fitting insulator 23 against the inside of magnetic core 11 by inserting the lower portion of conductor 17 upward into the core. The top portion 27 of conductor 17 may then be installed by threaded engagement with the lower portion 29, as illustrated in the cross-sectional view of FIG. 5.

In one embodiment, the length of magnetic core 11 may be on the order of about 5 to 10 mm, with a pole thickness of about 3 to 5 mm. Other dimensional values and design constraints for magnetic core 11 are possible within the scope of the invention, and will vary according to the particular application. For example, in an application for transmural RF ablation of an atrium, the design basis for magnetic core 11 ensures that the core is moveable along the surface of an atrial wall having an average thickness between about 3 mm and about 5 mm, and that a complementary pair of cores positioned on opposite sides of the atrial wall generates sufficient mutual magnetic force to urge the pair into symmetrical alignment. To facilitate movement along a surface of operative tissue such as an atrial wall, magnetic core 11 may be formed with one or more rounded corners 14, and may also be formed with a smooth surface at any point that may come into contact with tissue.

Figure 6:
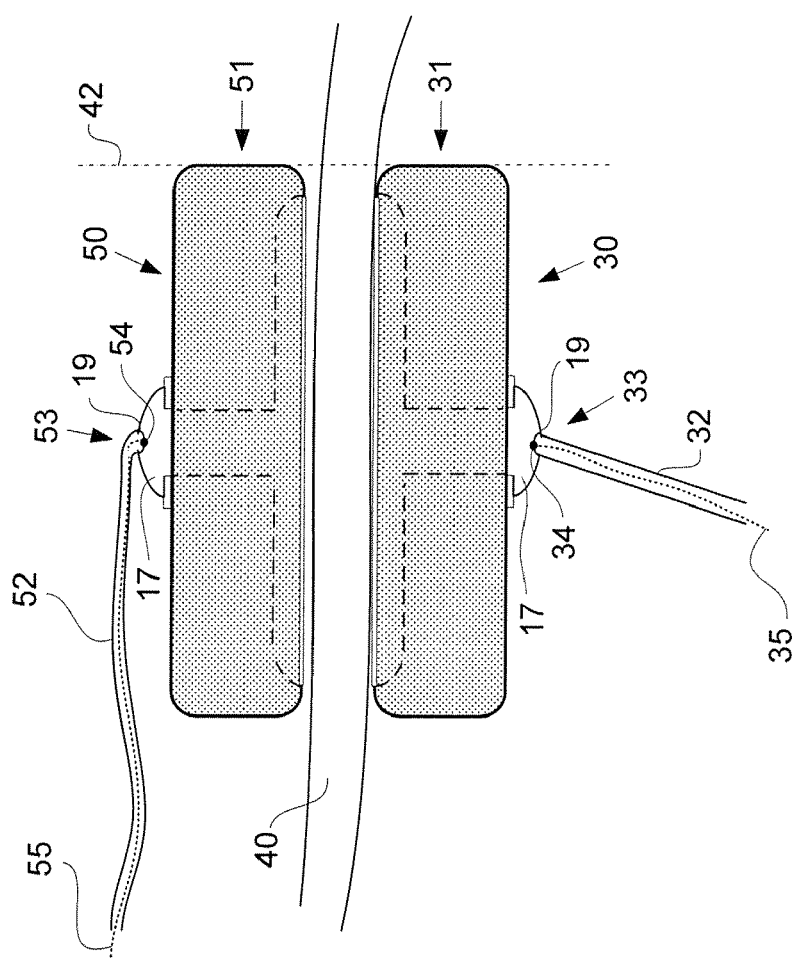
FIG. 6 is a side view of a magnetically coupled device having U-shaped magnets according to the invention positioned for transmural ablation of an atrium. An endocardial electrode is shown contacting the atrial wall and aligned with and facing an epicardial electrode that is contacting an opposite side of the atrial wall.

FIG. 6 illustrates a magnetically coupled device according to the invention positioned for transmural ablation of an atrium. The device consists of two complementary electrode assemblies having U-shaped magnetic cores. Preferably, each electrode assembly has a construction similar to electrode assembly 100. Alternatively, one electrode assembly may include a magnetic core that is a permanent magnet, while the complementary electrode assembly may include a magnetic core that is a demagnetized magnetic material. In FIG. 6, an endocardial electrode assembly 30 is shown contacting an atrial wall 40 and facing an epicardial electrode assembly 50 that is contacting an opposite side of the atrial wall. FIG. 7 shows a magnified side view of the same magnetically coupled device. The orientation of the electrode assemblies in FIGS. 6 and 7 is an optimal alignment for transmission.

In the optimal alignment for transmission, sides 31 and 51 of the cores lie substantially in the same plane 42. Similarly, sides 22 and 32 lie substantially in the same plane 44. In their respective figures, planes 42 and 44 are normal to the page, and each is indicated by a straight line. With electrode assemblies 30 and 50 in optimal alignment, transmitting elements 21 face each other across the atrial wall with a minimal volume of tissue between them. Optimal alignment thus also corresponds to the orientation that provides a minimum electrical resistance between electrodes along any segment of the atrial wall.

With reference again to FIG. 6, mechanical linkage of the electrode assemblies 30 and 50 to intracorporeal positioning devices are now described. According to the invention, the mechanical linkage may be either rigid or flexible. Various embodiments are possible in which both linkages may be rigid, in which both linkages may be flexible, or in which one linkage may be rigid and the other linkage may be flexible. In the embodiment shown in FIG. 6, linkage 32 is a rigid linkage connected to endocardial electrode assembly 30, and linkage 52 is a flexible linkage connected to epicardial electrode 50.

Linkage 32 may be a solid rod or hollow tube formed from biocompatible plastic or metal suitable for intravenous or subcutaneous use, similar to that used in the construction of catheters. Linkage 32 can be, for example, a rigid positioning device such as a catheter with a remotely positionable end. In one embodiment, linkage 32 may be an arm extending from conductor 17 and connectable to a subcutaneous probe or an intravenous catheter. Preferably, linkage 32 is hollow to allow one or more wires 35 to pass within the linkage and connect electrically to conductor 17. The distal end 33 of linkage 32 may connect mechanically to conductor 17 at or around wire receiving terminal 19 by welding, adhesion, or other fastening means. Wire 35 may connect to conductor 17 at a connection or soldering point 34 at wire receiving terminal 19.

Other connection arrangements are possible within the scope of the invention. For example, distal end 33 of linkage 32 may connect directly to the magnetic core, or to a plate or bracket (not shown) fixed elsewhere on the surface of electrode assembly 30. In another embodiment, wire 35 may run through a separate lumen in linkage 32, or may run externally to the mechanical linkage.

Whatever the arrangement, mechanical linkage 32 allows a surgeon to manipulate the position of electrode assembly 30 within the atrium or other intracorporeal location. When moved into an approximate desired location, e.g. within the atrium near the pulmonary veins, linkage 32 allows the surgeon to translate electrode assembly 30 along the atrial wall while maintaining contact therewith to finely adjust its position. In one embodiment, the linkage-to-electrode interface may include a mechanism such as a ball joint (not shown) to allow adjustment of electrode position with respect to the linkage with three degrees of freedom. It is also contemplated that the positioning of the electrode assembly may be accomplished with the aid of a video imaging device such as an endoscope introduced through a subxiphoid port.

Linkage 52 is illustrated as a flexible rod or flexible hollow tube formed from biocompatible plastic or metal suitable for intravenous or subcutaneous use. In one embodiment, linkage 52 may be a flexible extension connectable to a subcutaneous probe or an intravenous catheter with sufficient slack to avoid undue constrainment of the electrode assembly, and to provide three degrees of freedom for movement of electrode position with respect to the linkage. Preferably, linkage 52 is hollow to allow one or more wires 55 to pass within the linkage and connect electrically to conductor 17. For example, linkage 52 may comprise a layer of biocompatible insulation, such as teflon, that surrounds conductor 17. The distal end 53 of linkage 52 may connect mechanically to conductor 17 at or around wire receiving terminal 19 by welding, adhesion, or other fastening means. Wire 55 may connect to conductor 17 at a connection or soldering point 54 at wire receiving terminal 19. Other connection mechanical and electrical connections are possible, as discussed in the context of linkage 32.

The flexible characteristic of linkage 52 combined with the mutual magnetic attraction between electrode cores allows electrode assembly 50 to automatically position itself into optimal alignment on the outer atrial wall (or other intracorporeal location) without having to be directly manipulated by a surgeon. When manually introduced to an approximate desired location, e.g. on the outer atrial wall near the pulmonary veins, linkage 52 tracks the movement of its complementary electrode assembly while maintaining contact with the operative tissue. In this manner, an ablation device according to the invention optimally aligns opposing bipolar electrodes automatically, thereby maintaining dynamic alignment of the electrical conductors and improving the precision of ablation. Moreover, the invention gives the surgeon the ability to align bipolar electrodes with one hand, thereby reducing the complexity of the procedure and advantageously freeing the other hand to manipulate some other surgical instrument or device.

Figure 14:
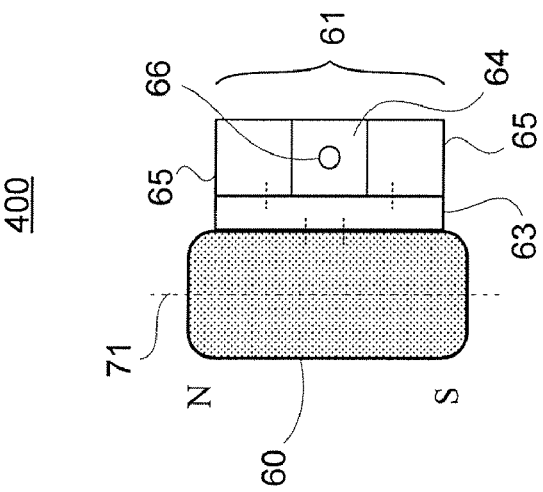
FIG. 14 is a top view of another embodiment of a magnetic electrode assembly for performing RF ablation according to the invention, wherein an elongated transmitting element lies parallel to a slideable bar magnet.

Turning now to FIG. 7, the electrical and magnetic interactions between electrode assemblies 30 and 50 are now described. In optimal alignment, the magnetic flux lines 45 of the magnetic cores pass from the north poles N to the south poles S in the directions shown, and the mutual magnetic force acts in the same general directions to pull the transmitting elements 21 into close proximity on opposite sides of the operative tissue. During an ablation procedure, wires 35 and 55 are connected to opposite electrical terminals of an RF generator 90 (FIG. 14). With electrode assemblies 30 and 50 in optimal alignment, the RF circuit is completed through the operative tissue. In this example, the operative tissue includes the portion of atrial wall 40 that borders transmitting elements 21. As the electric current is applied, adjacent ions within the tissue begin to oscillate at the same frequency as the RF current. These ions experience opposing frictional forces, and the resulting thermal energy elevates the ambient temperature around the transmitting elements causing coagulation necrosis and cellular damage at temperatures between about 50° C. and about 100° C.

Typically, the RF current needed to damage heart tissue at these temperatures must be sustained for a duration of about 60 seconds in the range of about 500 mA to about 1 A, rms. This current oscillates in conductors 17 at about 500 MHz in the directions indicated by the double-arrow line 44, creating magnetic flux lines 46. The electrode assemblies are configured so that magnetic flux resulting from the flow of electrons will lie in planes normal to flux lines 45. This helps to ensure that magnetic flux 46 will have negligible effect on the magnetic forces acting to maintain the electrodes in optimal alignment. In preferred embodiments of the invention, the strength of the magnetic field created by the complementary cores will dominate any additional magnetic effects introduced by the RF current or by a DC component superimposed on the RF current.

Other configurations of a magnetic core for an electrode assembly are possible within the scope of the invention. For example, in another embodiment, the magnetic core 11 may form a V-shaped trough, with two legs extending from a central notch at a separation angle of about 90 degrees. In such as embodiment, electrical conductor 17 may pass through the central notch area. Additional embodiments of the invention are disclosed in the following paragraphs.

FIG. 8 is a top view of an embodiment of a magnetic electrode assembly 200 for performing RF ablation according to the invention. In assembly 200, the magnetic core 60 forms a slideable cylindrical bar magnet have a north pole N and a south pole S as indicated, and a longitudinal axis 71 therebetween. The outer surface of magnetic core 60 is preferably smooth throughout. An electrical conductor 61 is bonded (or mechanically coupled) to and electrically insulated from core 60, and may extend in a direction generally perpendicular to the longitudinal axis 71 of the cylindrical bar magnet. The mechanical coupling may be effected by any conventional means. In assembly 200, core 60 is shown mechanically coupled to conductor 61 by one or more fasteners 62, which may be studs, pins, rivets, or threaded screws. A firm dielectric material 63 may be used to insulate conductor 61 from core 60. One or more additional fasteners 62 may be used to connect the insulation 63 to conductor 61. The magnetic, conductive, and dielectric materials of assembly 200 may be selected from stock similar to that disclosed above for electrode assembly 100.

Assembly 200 can be further understood with reference to the bottom view of FIG. 9, the end view of FIG. 10, and the side view of FIG. 11. Electrical conductor 61 may further include a wire receiving terminal 64 and a transmitting element 65. Wire receiving terminal 64 may provide a post, a planar area, or a recessed area for soldering a wire to conductor 61, or a male or female connection for coupling to a complementary plug or receptacle. In the embodiment shown, wire receiving terminal 64 provides a recessed area 66 for wire connection. In one embodiment, conductor 61 may be cast or machined as a single metal part.

The bottom edge of the cylindrical core 60 forms a coupling surface 68 for magnetically coupling to a complementary core. At all times during movement of coupling surface 68, the transmitting element 65 remains adjacent and in fixed relation to coupling surface 68. A rigid mechanical linkage 67 is provided at the top of conductor 61 to link assembly 200 to an intracorporeal positioning means capable of guiding or sliding the coupling surface 68 along a surface of operative tissue. In a complementary electrode assembly, rigid mechanical linkage 67 may be replaced with a flexible mechanical linkage 69.

FIG. 12 illustrates a side view of a magnetically coupled device having cylindrical bar magnets in optimal position for transmural ablation of an atrium. The device consists of a complementary pair of slideable electrode assemblies similar in construction to assembly 200. An endocardial electrode assembly 72 is shown contacting an atrial wall 40 and aligned with and facing an epicardial electrode assembly 74 that is contacting an opposite side of the atrial wall. As previously described, the device is in optimal position for transmural ablation when assembly 72 is directly opposite assembly 74 so that transmitting elements 65 can create a linear ablation in the tissue when energized.

In this embodiment, the alternating electric field 44 is offset from the area of greatest magnetic force, Fm, lying directly between the magnetic cores. This offset, combined with the dominant strength of the magnetic field created by the complementary cores renders negligible any additional magnetic effects introduced by RF or DC current flowing through conductors 61. Otherwise, the operating principles of the device of FIG. 12 are similar to the device of FIG. 7. During translation of electrode assembly 72 along tissue wall 40, mutual magnetic attraction causes electrode assembly 74 to track automatically the position of assembly 72 to maintain optimal dynamic alignment of the electrical conductors while ablating the tissue.

Figure 13:
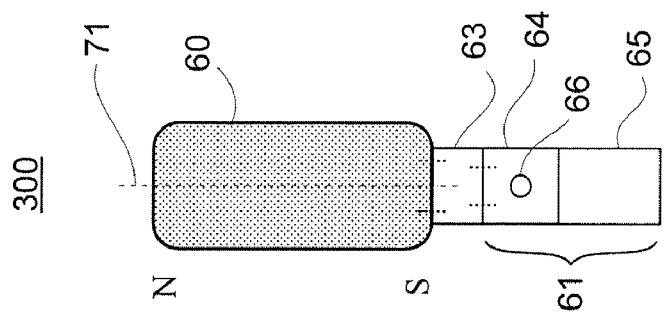
FIG. 13 is a top view of another embodiment of a magnetic electrode assembly for performing RF ablation according to the invention, wherein a trailing elongated transmitting element is concentrically with a slideable bar magnet.

FIG. 13 illustrates another embodiment, 300, of an electrode assembly according to the invention. This assembly includes components similar to those of assembly 200, and operates in similar fashion. The main difference is the orientation of electrical conductor 61 with respect to the magnetic core 60. Conductor 61 forms an elongated transmitting element or elongated conductive segment that at one end is bonded to and electrically insulated from core 60. Conductor 61 is oriented generally concentrically with longitudinal axis 71 and extends from core 60 in the longitudinal direction. As electrode assembly 300 is moved along a tissue wall, conductor 61 trails behind core 60 in concentric alignment therewith.

FIG. 14 illustrates another embodiment, 400, of an electrode assembly according to the invention. This assembly includes components similar to those of assembly 200, and operates in similar fashion. In assembly 400, electrical conductor 61 forms an elongated conductive segment that is oriented generally parallel to the longitudinal axis 71 of magnetic core 60. Conductor 61 lies adjacent to core 60, and is bonded to and electrically insulated from the core by an insulator 63, using an adhesive, fasteners, or other means for connection. As electrode assembly 400 is moved along a tissue wall, conductor 61 rides alongside the core, generally parallel to axis 71.

Figure 15:
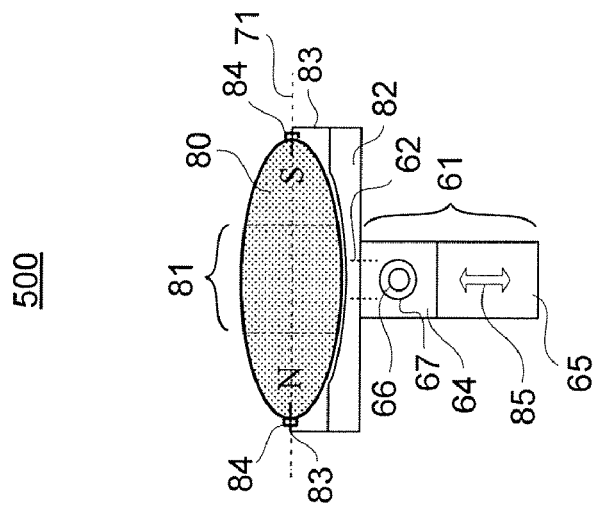
FIG. 15 is a top view of another embodiment of a magnetic electrode assembly for performing RF ablation according to the invention, wherein the magnetic core forms a rolling ellipsoidal bar magnet.

FIG. 15 illustrates magnetic electrode assembly 500, which is another embodiment of the invention for performing precision RF ablation. Assembly 500 includes a rolling or rotatable substantially cylindrical bar magnet 80 having a smooth outer surface. A central area of the outer surface constitutes a circumferential magnetic coupling surface 81. In one embodiment, bar magnet 80 may have an ellipsoidal shape and volume. An electrical conductor 61 is mechanically coupled to and electrically insulated from magnet 80, and includes a wire receiving terminal 64 and a transmitting element 65. Wire receiving terminal 64 includes a means 66 for electrically coupling an external wire to conductor 61. A mechanical linkage 67 connects assembly 500 to an intracorporeal positioning device. At all times during translation of the device and rotation of bar magnet 80, transmitting element 65 remains adjacent to a portion of the central area of the circumferential magnetic coupling surface 81.

Electrical insulation between bar magnet 80 and conductor 61 is provided by a dielectric insulator 82. The insulator 82 is preferably rigid so that it may be reliably mechanically fastened to conductor 61 using one or more fasteners 62. In addition, insulator 82 supports one or more axles 83 and one or more bearings 84. Axles 83 and bearings 84 allow bar magnet 80 to rotate freely about a central longitudinal axis 71 so that the assembly may roll or be rolled along the surface of operative tissue.

The agility of electrode assembly 500 provides a notable advantage when positioning the device for ablation. Its ability to roll rather than slide across irregular areas of tissue wall, combined with the gradual curvature of its ellipsoidal surface make translation of the leading (rigidly linked) electrode across the operative tissue less susceptible to obstruction, while allowing the following (flexibly linked) electrode to more easily work its way into optimal alignment. In optimal alignment, the magnetic coupling surfaces 81 of the complementary pair are in direct opposition. In all other respects, when magnetically coupled to a complementary electrode assembly, operation of electrode assembly 500 during an ablation procedure is similar to the operation of assemblies 100 and 200.

Figure 16:
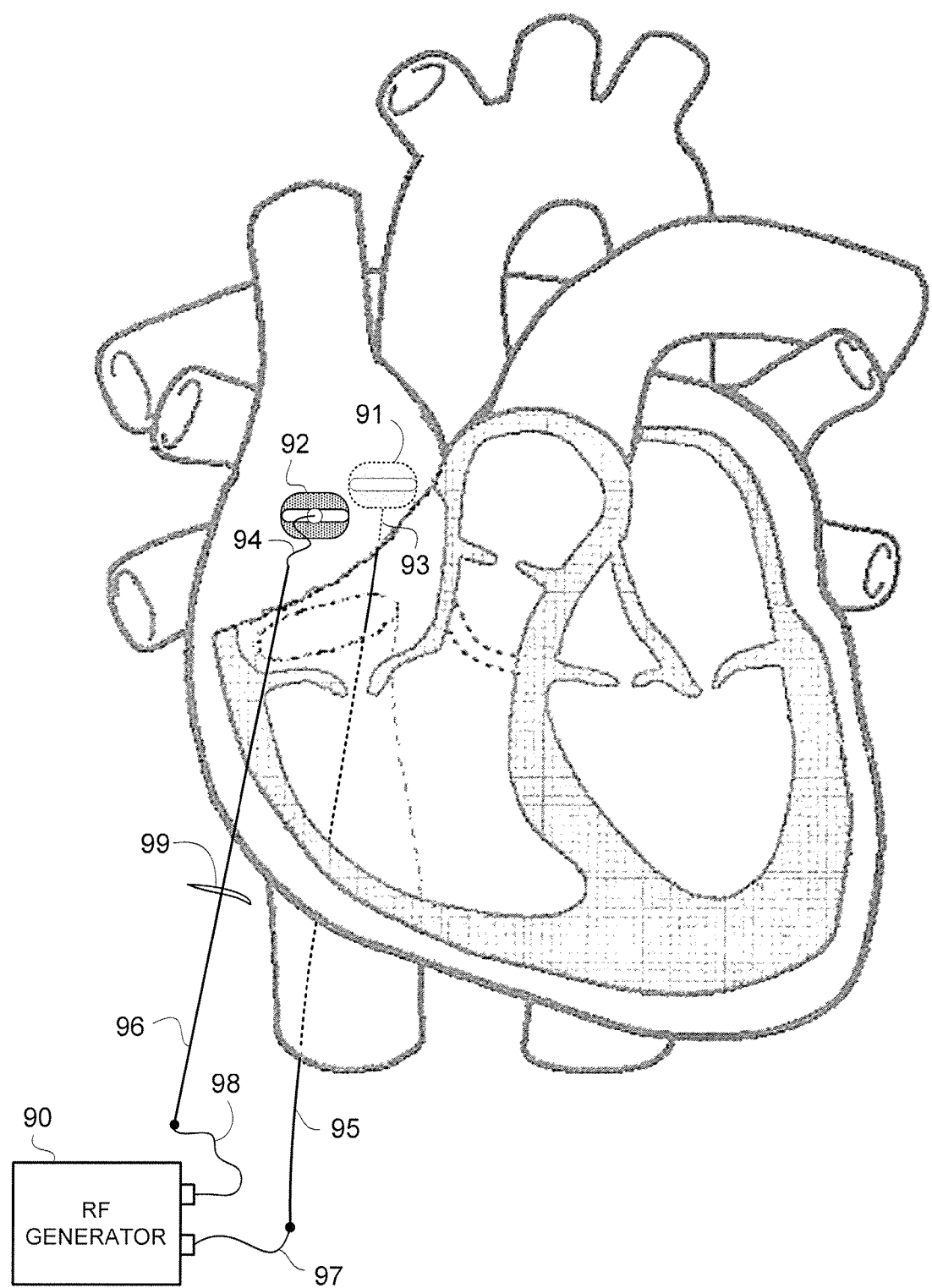
FIG. 16 is a frontal partial cutaway view of a human heart, showing a magnetically coupled ablation device positioned on opposite walls of the right atrium.

FIG. 16 is a conceptual illustration showing a magnetically coupled ablation device according to the invention positioned on opposite walls of the right atrium of a human heart. The right atrium is shown only for purposes of illustrating procedural use of the invention, and is not meant to limit application thereof. For example, the invention has particular application in performing a maze procedure on the left atrium for isolating the pulmonary veins.

An endocardial electrode assembly 91 is equipped with a rigid mechanical linkage 93. Linkage 93 is coupled to an intracorporeal positioning device 95, preferably a stiff or somewhat flexible rod, hollow rod, or catheter. A wire 97 coupled to a wire receiving terminal on electrode assembly 91 runs through or along linkage 93 and positioning device 95, to a first terminal on an RF generator 90. An epicardial electrode assembly 92 is equipped with a flexible mechanical linkage 94. Linkage 94 is coupled to a second intracorporeal positioning device 96, which is also preferably a stiff or somewhat flexible rod or catheter. A second wire 98 is coupled to a wire receiving terminal on electrode assembly 92, and runs through or along linkage 94 and positioning device 96, to a second terminal on RF generator 90 to complete the circuit. The second terminal has an electrical polarity opposite that of the first terminal. RF generator 90 may be a 200 W, 500 kHz to 1 MHz, 120/240VAC unit such as a Boston Scientific model RF-3000 generator or equivalent. Wires 97 and 98 are sized appropriately to carry load current expected from such a device, and the wire receiving terminals on the electrode assemblies are configured for accommodating this size of wire.

The system is arranged so that a surgeon may initially position electrode assemblies 91 and 92 to approximate intracorporeal locations using minimally invasive techniques. For example, when positioning the device for transmural ablation of an atrial wall, assemblies 91 and 92 may be guided initially using hand-held or automatic intracorporeal positioning devices 95 and 96, respectively. Electrode 91 is shown positioned intravenously through the inferior vena cava to a location within the right atrium. Electrode 92 is shown positioned percutaneously through a small incision 99 made through the thoracic wall to a location on the outside of the right atrium. The length of positioning devices 95 and 96 will vary depending on type and application.

In achieving the initial approximate locations, it is contemplated that the surgeon will manually or automatically cause positioning devices 95 and 96 to transport the electrodes, simultaneously or one at a time, and preferably with the aid of one or more imaging devices providing live video feedback, until each electrode reaches a point close to the operative tissue. For example, when positioning the epicardial electrode, an endoscope may be used to provide a video image of the electrode and the surrounding tissue. When positioning the endocardial electrode, its position may be determined using fluoroscopy or its position may be inferred from electrical activity. An MRI or other image of the operative tissue, developed in advance of surgery, may be used as a map to assist the surgeon in identifying the correct approximate location for each electrode. When the approximate positions are achieved, the complementary electrode pair will be compelled into optimal alignment through mutual magnetic attraction, as previously described. At this point, the surgeon may proceed by making fine adjustments in the position of the leading electrode assembly to properly align it along a desired ablation path. For this purpose, an electrode assembly according to the invention may further include a guiding feature, such as a distinctive line or arrow 85 (FIG. 15) made from material easily discernable through the live video image that indicates to the surgeon the orientation of the transmitting element. This will assist the surgeon in properly orienting the electrode to draw an ablation scar along a desired pathway.

When the electrodes are in optimal alignment along the desired pathway, the surgeon may cause RF generator 90 to energize the electrical circuit and begin the process of burning transmural lesions into the tissue. After sufficient time has elapsed (usually about 1 minute, depending on heat transfer), the surgeon may deliberately cause the leading electrode to move further along the desired pathway so that the following electrode tracks the movement and maintains the device in optimal alignment, without excessive overlapping of tissue already burned. The procedure may be performed using continuous or intermittent application of RF current, and may be continued until a desire maze pattern has been achieved. In one application, a skilled surgeon may control the operation by guiding the complementary electrodes slowly and continuously along a desired burn path while continuously or intermittently applying RF current over the course of electrode movement.

Electrode assemblies 91 and 92 are each depicted as having a trough-type core similar to assembly 100. However, either or both electrode assemblies 91 and 92 may comprise alternative configurations according to the principles herein disclosed, such as one that incorporates a slideable cylindrical core, as shown in assembly 200, or one that incorporates a rotatable ellipsoidal core, as shown in assembly 300, or some other configuration of an electrode assembly having a magnetic coupling surface electrically insulated from an electrical conductor having a wire receiving terminal and a transmitting element adjacent to the magnetic coupling surface, and a mechanical linkage to an intracorporeal positioning device.

The invention may be used in connection with an external control system (not shown) that controls energy transmission between the transmitting elements of the electrode assemblies. The control system may provide an optional safety feature that prohibits transmission of energy unless the ablation device is in optimal or near optimal alignment. One embodiment of this feature may be a current-limiting feature that interrupts the circuit when the peak current exceeds a predetermined threshold. Another embodiment of this feature may be a voltage-limiting feature that interrupts the circuit when the peak voltage required to sustain current flow between the electrodes exceeds a predetermined threshold. Another embodiment of this feature may rely on a proximity sensor located on one or both of the complementary electrode assemblies that senses an optimal alignment condition or absence thereof. For example, an electrode assembly may include a miniaturized reed switch that changes electrical state in response to a magnetic field strength that exists only when both complementary cores are closely or optimally aligned. A DC signal indicating the position of the reed switch may be superimposed on a wire carrying RF, or an additional isolated wire may threaded through the intracorporeal positioning device to carry the reed switch signal to the external control system. In this fashion, the control system can independently verify whether the ablation device is in optimal alignment, and allow energy transmission only when this condition exists. The safety feature thereby helps to prevent unnecessary damage to tissue surrounding the desired ablation path.

It is also contemplated that an electrode assembly according to the invention may include one or more inductive conductors oriented with respect to the magnetic core to form an electromagnet, such that energization of the inductive conductor with a DC current amplifies the magnetic field. This design would advantageously allow for adjustment of the magnetic field strength by the control system. For example, if the electrode assemblies are having difficulty aligning due to gravity, atrial wall topography, or some other obstruction, the control system may temporarily boost the strength of the magnetic field by adding or elevating DC current flow through the inductive conductor, up to a safe limit, until acceptable alignment is achieved. An additional isolated wire may be provided for energizing the inductive conductor. The control system may also allow the temporary boost to be initiated through manual action.

The invention has been disclosed in an illustrative style. Accordingly, the terminology employed throughout should be read in an exemplary rather than a limiting manner. Although minor modifications of the present invention will occur to those well versed in the art, it shall be understood that what is intended to be circumscribed within the scope of the patent warranted hereon are all such embodiments that reasonably fall within the scope of the advancement to the art hereby contributed, and that that scope shall not be restricted, except in light of the appended claims and their equivalents.

What is claimed is:

1. An electrode assembly for ablation of operative tissue, comprising:
    a magnetic core having a magnetic coupling surface, and having a first portion and a second portion;
    an ablative electrode coupled to and electrically insulated from the magnetic core, the ablative electrode having a wire receiving terminal and a transmitting element, the transmitting element adjacent the magnetic coupling surface, wherein the ablative electrode is positioned at least partially between the first portion and the second portion of the magnetic core; and
    an electrical insulation electrically insulating the ablative electrode from the magnetic core.

2. The electrode assembly of claim 1 wherein the magnetic coupling surface comprises a smooth surface with a rounded edge.

3. The electrode assembly of claim 1 wherein the magnetic core comprises a trough.

4. The electrode assembly of claim 3 wherein the trough is U-shaped with a cross member connecting two substantially parallel legs and the electrical conductor passes through the cross member.

5. The electrode assembly of claim 3 wherein the trough is V-shaped with two legs extending from a central notch at a separation angle of about 90 degrees and the ablative electrode passes through the central notch.

6. The electrode assembly of claim 1 wherein the transmitting element further comprises an elongated conductive segment.

7. The electrode assembly of claim 6 wherein the elongated conductive segment lies in a direction parallel to the magnetic coupling surface.

8. The electrode assembly of claim 1 wherein magnetic flux lines leaving the magnetic coupling surface point in a direction substantially normal to magnetic flux lines created by an electric current flowing directly from the wire receiving terminal to the transmitting element.

9. The electrode assembly of claim 1 wherein the wire receiving terminal on the ablative electrode is configured for terminating a transmission wire sized for carrying RF current for bipolar ablation of an atrial wall.

10. The electrode assembly of claim 1, further comprising a rigid positioning device connected to the ablative electrode through a connection which allows a rotational freedom between an orientation of the rigid positioning device and an orientation of the ablative electrode.

11. The electrode assembly of claim 1 wherein the rigid positioning device is a catheter with a remotely positionable end.

12. A magnetically coupled device for transmural ablation of operative tissue, comprising:
    a first electrode assembly including
        a first permanent magnetic core having a magnetic coupling surface, and having a first portion and a second portion,
        a first ablative electrode positioned at least partially between the first portion and the second portion of the first permanent magnetic core, the first ablative electrode having an elongated transmitting surface, and
        a first linkage having a connection to the ablative electrode,
        wherein the first linkage is a rigid positioning device and the connection between the first linkage and the ablative electrode allows rotational freedom between an orientation of the first linkage and an orientation of the first ablative electrode; and
    a second electrode assembly including
        a second permanent magnetic core having a magnetic coupling surface, and having a first portion and a second portion,
        a second ablative electrode positioned at least partially between the first portion and the second portion of the second permanent magnetic core, the second ablative electrode having an elongated transmitting surface, and
        a second linkage having a connection to the second ablative electrode,
        wherein when the magnetic coupling surface of the first permanent magnetic core and the magnetic coupling surface of the second permanent magnetic core are positionable on opposing sides of the operative tissue, mutual magnetic attraction therebetween properly aligns the first ablative electrode and the second ablative electrode for bipolar ablation.

13. The magnetically coupled device of claim 12 wherein the the second linkage is a flexible positioning device.

14. The magnetically coupled device of claim 13 wherein when the magnetic coupling surface of the first permanent magnetic core and the magnetic coupling surface of the second permanent magnetic core are positionable on opposing sides of the operative tissue, movement of the first electrode assembly by the rigid positioning device causes the second electrode assembly to track the first electrode assembly automatically to maintain dynamic alignment of the first ablative electrode and the second ablative electrode.

15. The magnetically coupled device of claim 12 wherein the rigid positioning device is a catheter with a remotely positionable end.

16. A medical device for heat ablation of an atrial wall comprising:
   a first electrode assembly comprising
      a first permanent magnetic core,
      a first ablative electrode located adjacent the first permanent magnetic core, and
      a first linkage connected to the first ablative electrode through a first connection,
   wherein the first connection allows rotational freedom between an orientation of the first linkage and an orientation of the first ablative electrode, wherein the first linkage is a rigid positioning device; and
   a second electrode assembly comprising
      a second permanent magnetic core,
      a second ablative electrode located adjacent the second permanent magnetic core, wherein current is passed through the first ablative electrode and the second ablative electrode for ablating the atrial wall, and the second ablative electrode is automatically aligned with the first ablative electrode when positioned on opposing sides of the atrial wall, and
      a second linkage connected to the second ablative electrode through a second connection,
   wherein the position of the first electrode assembly is manipulated by the first linkage and the position of the second ablative electrode is unconstrained by the second linkage and moves in response to manipulation of the first linkage.

17. The medical device of claim 16 wherein the first electrode assembly or the second electrode assembly is configured to ablate the atrial wall when the first electrode assembly is in a fixed position on the atrial wall.

18. The medical device of claim 16 wherein the first electrode assembly or the second electrode assembly is configured to ablate the atrial wall when the first electrode assembly is moving along the atrial wall.

19. The medical device of claim 16 wherein the first ablative electrode further includes an elongated transmitting surface that is configured to create a substantially linear ablation pattern in the atrial wall when an electrical current is passed between the first ablative electrode and the second ablative electrode without moving the first electrode assembly.

20. The medical device of claim 19 wherein the elongated transmitting surface has a width of 1 mm or less.

21. The medical device of claim 16 wherein the first permanent magnetic core is configured to rotate relative to the orientation of the first ablative electrode.

22. The medical device of claim 16 wherein the first electrode assembly further comprises a proximity sensor that senses an alignment between the first ablative electrode and the second ablative electrode.

23. The medical device of claim 16 wherein the rigid positioning device is a catheter with a remotely positionable end.

* * * * *